US007586957B2

(12) United States Patent
Sierra et al.

(10) Patent No.: US 7,586,957 B2
(45) Date of Patent: Sep. 8, 2009

(54) PICOSECOND LASER APPARATUS AND METHODS FOR ITS OPERATION AND USE

(75) Inventors: Rafael Armando Sierra, Palmer, MA (US); Mirko Mirkov, Chelmsford, MA (US); Richard Shaun Welches, Manchester, NH (US)

(73) Assignee: Cynosure, Inc, Westford, MA (US)

( * ) Notice: Subject to any disclaimer, the term of this patent is extended or adjusted under 35 U.S.C. 154(b) by 37 days.

(21) Appl. No.: 11/461,812

(22) Filed: Aug. 2, 2006

(65) Prior Publication Data

US 2008/0031288 A1 Feb. 7, 2008

(51) Int. Cl.
*H01S 3/115* (2006.01)
(52) U.S. Cl. .............................. 372/12; 372/10; 372/11; 372/17; 372/25; 372/30
(58) Field of Classification Search .............. 372/38.03, 372/10–18, 25, 30
See application file for complete search history.

(56) References Cited

U.S. PATENT DOCUMENTS

| 4,375,684 | A * | 3/1983 | Everett ........................ 372/18 |
| 2002/0167974 | A1 * | 11/2002 | Kennedy et al. .............. 372/10 |
| 2005/0074038 | A1 * | 4/2005 | Khaydarov .................. 372/11 |

* cited by examiner

*Primary Examiner*—Minsun Harvey
*Assistant Examiner*—Tod T Van Roy (57) ABSTRACT

Apparatuses and methods are disclosed for applying laser energy having desired pulse characteristics, including a sufficiently short duration and/or a sufficiently high energy for the photomechanical treatment of skin pigmentations and pigmented lesions, both naturally-occurring (e.g., birthmarks), as well as artificial (e.g., tattoos). The laser energy may be generated with an apparatus having a resonator with the capability of switching between a modelocked pulse operating mode and an amplification operating mode. The operating modes are carried out through the application of a time-dependent bias voltage, having waveforms as described herein, to an electro-optical device (e.g., a Pockels cell) positioned along the optical axis of the resonator.

26 Claims, 4 Drawing Sheets

PICOSECOND LASER APPARATUS AND METHODS FOR ITS OPERATION AND USE

FIELD OF THE INVENTION

The present invention relates to apparatuses and methods for delivering laser energy having a short pulse duration (e.g., less than about 1 nanosecond) and high energy output per pulse (e.g., greater than about 250 millijoules). The desired operating parameters are achieved through the application of a bias voltage, having a time-dependent value as described herein, to an electro-optical device such as a Pockels cell. The Pockels cell may be disposed in a single laser having a resonator that can be operated in two modes, depending on the bias voltage applied to the electro-optical device. As a result, laser energy suitable for a number of applications, including treating and removing pigment particles such as those introduced to the human body as tattoos, may be generated using a relatively simple apparatus.

BACKGROUND OF THE INVENTION

Lasers are recognized as controllable sources of radiation that is relatively monochromatic and coherent (i.e., has little divergence). Laser energy is applied in an ever-increasing number of areas in diverse fields such as telecommunications, data storage and retrieval, entertainment, research, and many others. In the area of medicine, lasers have proven useful in surgical and cosmetic procedures where a precise beam of high energy radiation causes localized heating and ultimately the destruction of unwanted tissues. Such tissues include, for example, subretinal scar tissue that forms in age-related macular degeneration (AMD) or the constituents of ectatic blood vessels that constitute vascular lesions.

The principle of selective photothermolysis underlies many conventional medical laser therapies to treat diverse dermatological problems such as leg veins, portwine stain birthmarks, and other ectatic vascular and pigmented lesions. The dermal and epidermal layers containing the targeted structures are exposed to laser energy having a wavelength that is preferentially or selectively absorbed in these structures. This leads to localized heating to a temperature (e.g., to about 70° C.) that denatures constituent proteins or disperses pigment particles. The fluence, or energy per unit area, used to accomplish this denaturation or dispersion is generally based on the amount required to achieve the desired targeted tissue temperature, before a significant portion of the absorbed laser energy is lost to diffusion. The fluence must, however, be limited to avoid denaturing tissues surrounding the targeted area.

Fluence, however, is not the only consideration governing the suitability of laser energy for particular applications. The pulse duration and pulse intensity, for example, can impact the degree to which laser energy diffuses into surrounding tissues during the pulse and/or causes undesired, localized vaporization. In terms of the pulse duration of the laser energy used, conventional approaches have focused on maintaining this value below the thermal relaxation time of the targeted structures, in order to achieve optimum heating. For the small vessels contained in portwine stain birthmarks, for example, thermal relaxation times and hence the corresponding pulse durations of the treating radiation are often on the order of hundreds of microseconds to several milliseconds.

The use of even shorter pulses, however, results in a change from photothermal to photomechanical processes. The latter mechanism is invoked by applying laser pulses having a duration that is below the acoustic transit time of a sound wave through targeted particles. This causes pressure to build up in the particles, in a manner analogous to the accumulation of heat within a target irradiated by laser pulses having a duration that is below the thermal relaxation time.

Photomechanical processes described above can provide commercially significant opportunities, particularly in the area of treating skin pigmentations including tattoos, portwine stains, and other birthmarks. The incidence of tattoos in the U.S. tattoo pigment particles of about 1 micron in diameter or less may be cleared from the body via ordinary immune system processes, stable tattoos are likely composed of pigment particles having diameters on the order of 1-10 microns or more. As the speed of sound in many solid media is approximately 3000 meters/second, the acoustic transit time across such particles, and consequently the laser pulse duration required to achieve their photomechanical destruction, is as low as hundreds of picoseconds. The acoustic transit time of a sound wave in a particle is calculated by dividing the radius of the particle by the speed of sound in the particle.

In addition to such short pulse durations, high energy laser pulses are needed for significant disruption of tattoo pigment particles and other pigmentations. Required fluences of several joules per square centimeter and treatment spot sizes of a few millimeters in diameter translate to a desired laser output with several hundred millijoules (mJ) per pulse or more. Unfortunately, current systems capable of such short pulse duration and high energy output are too complex and/or expensive for practical use in the treatment or removal of tattoos and other pigmentations. These devices generally require two or more lasers and amplifier stages, together with multiple electro-optical and/or acousto-optic devices.

Sierra and Russell (SBIR Proposal to the NIH, submitted December 1993) disclose a device of reduced complexity, which demonstrated 100 millijoules of output. The device uses a single laser gain medium that is common to two resonators. A Pockels cell is used to sequentially select one or the other of the two resonators. Operation requires applying a bias voltage to the Pockels cell to establish a modelocked pulse along the first resonator, switching the Pockels cell bias voltage to amplify the pulse along a second, separate resonator, and then switching the Pockels cell bias again to extract the amplified pulse. The gain or lasing medium, two polarizers, a Pockels cell, an acousto-optical device, and two mirrors are included along the optical pathway of the first resonator. The lasing medium, polarizers, electro-optical device, and an additional mirror are included along the optical pathway of the second resonator.

While this apparatus is less complex than multiple laser systems, it nevertheless requires a large number of optical components (e.g., seven or more). In addition, the voltages applied and switched at the Pockels cell are equal to the halfwave bias voltage of the Pockels cell, typically in excess of 5,000 volts. These voltages must be switched in less than a few nanoseconds, placing a significant demand on the switching electronics. Also, because the system utilizes the separate operation of two resonators, it is possible due to component limitations for radiation from one resonator to leak or "spill over" into another. A consequence of this is the generation of undesirable or "parasitic" pulses, particularly in the resonator used for amplification, which supports a significantly lower threshold for laser oscillation. Finally, the use of an acousto-optic modulator to achieve modelocking may require the constant adjustment of resonator length, as such devices operate only at discrete resonant frequencies.

The simpler alexandrite and other Q-switched lasers currently employed in the treatment of dermatological pigmentations cannot reliably achieve tattoo pigment particle clearance in a matter of only a few treatments, despite claims to the contrary. Consequently, there is a need in the art for laser apparatuses of relatively low complexity, such that they are practical for tattoo pigment particle removal and the treatment of other pigmented lesions. Such apparatuses, however, must also be capable of emitting laser radiation with the short pulse duration required to invoke photomechanical processes. As discussed above, this requires pulse durations on the order of several hundred picoseconds, or the acoustic transit time across targeted pigment particles. Also characteristic of such a device is the capability of achieving an output energy of several hundred millijoules or more.

BRIEF SUMMARY OF THE INVENTION

The present invention is associated with the discovery of methods and apparatuses described herein for delivering pulsed laser energy with pulse characteristics suitable for a number of practical applications. Such pulse characteristics include a sufficiently short duration and/or a sufficiently high energy for the photomechanical treatment of skin pigmentations and pigmented lesions, both naturally-occurring (e.g., birthmarks), as well as artificial (e.g., tattoos). Advantageously, rather than requiring at least two resonators (or laser cavities), pulsed laser energy having the desired characteristics may be generated, according to a particular embodiment of the present invention, with an apparatus having a single resonator and lasing (or gain) medium, together with an electro-optical device to effect switching between two different operating modes of the single resonator.

In addition to requiring only a single resonator and lasing (or gain) medium, apparatuses may be further simplified in that, in a first operating mode, a modelocked pulse is established in the resonator, without the use of an additional modelocking device such as an acousto-optic modulator. Moreover, the need to adjust resonator length, associated with the use of some acousto-optical devices, is eliminated. The overall component and operating requirements of apparatuses according to embodiments of the present invention are therefore considerably simplified. For example, in some cases only four optical components may be required, as is common in many Q-Switched laser systems.

These and other advantages are associated with the application, to an electro-optical device (e.g., a Pockels cell) positioned along the optical axis of the resonator, a time-dependent bias voltage having a periodic waveform with an amplitude to effect a first operating mode. In particular, the periodic waveform has a period substantially equal to the round trip time of laser energy oscillating in the resonator, which results in the generation of a modelocked pulse. Other aspects of the present invention include the electronics necessary to generate the time-dependent bias voltage described above, as well as optionally a baseline operating voltage and voltages for (A) implementing a second operating mode of the resonator which amplifies laser energy oscillating in the resonator and (B) thereafter extracting the amplified laser pulse, having the desired pulse duration and pulse energy characteristics.

In one embodiment, therefore, the present invention is a method for generating pulsed laser energy. The method comprises reflecting laser energy between two substantially totally reflective mirrors disposed at opposite ends of a resonator and through a polarizer and an electo-optical device within the resonator and positioned along the optical path (or longitudinal axis) of the resonator. A lasing (or gain) medium, for example a flashlamp pumped laser rod, is also positioned along the optical axis. The method further comprises applying to the electro-optical device a time-dependent bias voltage, $V(t)$, equal to the sum of a baseline voltage, $V_o$, and a time-dependent differential voltage, $\delta V(t)$. This time-dependent differential voltage varies periodically with a period substantially equal to twice the time required (i.e., the round trip time) for the laser energy to traverse the length of the resonator, allowing for operation in some cases without the need to make adjustments to the resonator length. The method may also involve setting or adjusting the amplitude of the time dependent differential voltage and/or pumping the lasing medium (e.g., using optical pumping means such as a flashlamp) under conditions sufficient to establish a modelocked pulse in the resonator. This provides a first mode of operation in the resonator.

In a subsequent, second mode of operation, the modelocked pulse is amplified. In the case where the electro-optical device is positioned between the polarizer and one of the mirrors (arbitrarily denoted the "second" mirror) a first (constant) bias voltage may be applied to the electro-optical device such that a pulse reflected at this second mirror traverses the polarizer substantially without loss of intensity or amplitude. To extract the energy from the amplified pulse, a second (constant) bias voltage may thereafter be applied to the electro-optical device such that the polarizer substantially expels a pulse reflected at the second mirror from the resonator. This releases the pulsed laser energy having the desired characteristics described herein.

The first bias voltage, for example, may be substantially 0 and the second bias voltage may be substantially equal to the quarter wave voltage of the electro-optical device. The baseline voltage, $V_o$, is generally from about 30% to about 70%, and often from about 40% to about 60%, of the quarter wave voltage of the electro-optical device. The time-dependent differential voltage, $\delta V(t)$, has an amplitude generally from about 5% to about 35%, and often from about 10% to about 30%, of the quarter wave voltage of the electro-optical device (e.g., Pockels cell). Advantageously, these voltages are one half or less than the halfwave voltage (required in known methods) and therefore result in a significant reduction in the switching electronics requirements.

The pulsed laser energy generated according to methods of the present invention may have at least about 100 mj/pulse, and often will have from about 200 to about 800 mj/pulse, as required for applications described herein, such as the removal or dispersion of pigment particles as often used to form tattoos. As is also desired in these applications, the pulsed laser energy generally has a pulse duration of at most about 500 picoseconds (ps), typically at most about 300 ps, and often at most about 150 ps. As stated previously, any of the methods described above may be performed without the need to adjust resonator length.

Other embodiments of the invention include laser apparatuses for performing any of the methods described above, and in particular for generating pulsed laser energy with pulses having a duration of at most about 500 ps and an energy or intensity of at least about 100 mj. A representative apparatus comprises a resonator having first and second mirrors, each of which is substantially totally reflective, disposed at opposite ends of the resonator. The apparatus also includes a lasing material (e.g., a solid state lasing medium), an electro-optical device (e.g., a Pockels cell), and a polarizer, all of which are positioned along the optical axis of the resonator. The electro-optical device is positioned on this axis between the polarizer and the (arbitrarily denoted) "second" mirror.

The bias voltage of the electro-optical device may be modified such that two operating modes, pulse modelocking and pulse amplification, are carried out sequentially, as described above, in a single resonator. Therefore, apparatuses according to some embodiments of the invention do not include a modelocking device such as an acousto-optic modulator. In other embodiments, the apparatuses may include a resonator, and often include a single resonator only, which is configured to generate laser radiation with the desirable pulse duration and energy characteristics as discussed herein. The resonator may be included in the apparatus, for example, in the absence of any other components that would materially affect its basic and novel characteristics.

An additional aspect of the present invention involves the use of voltage waveform generating electronics for applying the necessary voltage during operation to the electro-optical device, in order to invoke the separate and normally sequential operating modes of the apparatus, as described above. In particular embodiments, these waveform generating electronics apply a time-dependent bias voltage, $V(t)$, equal to the sum of a baseline voltage, $V_o$, and a time-dependent differential voltage, $\delta V(t)$. The time-dependent differential voltage varies periodically with a period substantially equal to the round trip time required for the laser energy in the resonator.

The voltage waveform electronics may be used for initially applying the baseline voltage, $V_o$, to the electro-optical device, prior to applying the time-dependent differential voltage, $\delta V(t)$, which establishes a first, modelocked operating mode, as discussed above. Subsequently, the voltage waveform electronics can apply a first (constant) bias voltage (e.g., zero voltage or complete discharge of the electro-optical device), such that a reflected pulse at the second mirror traverses the polarizer substantially without loss of intensity. Under these conditions the lasing or gain medium amplifies the laser energy within the resonator, in a second, amplification operating mode, prior to its extraction or release from the apparatus as laser energy having the desirable pulse characteristics, including the short pulse duration and high pulse energy discussed above. This generation of such laser energy, for applications discussed herein, is ultimately effected by applying a second bias voltage (e.g., the quarter wave voltage) to the electro-optical device, such that a pulse reflected at the second mirror is substantially expelled from the resonator at the polarizer.

Figure 4:
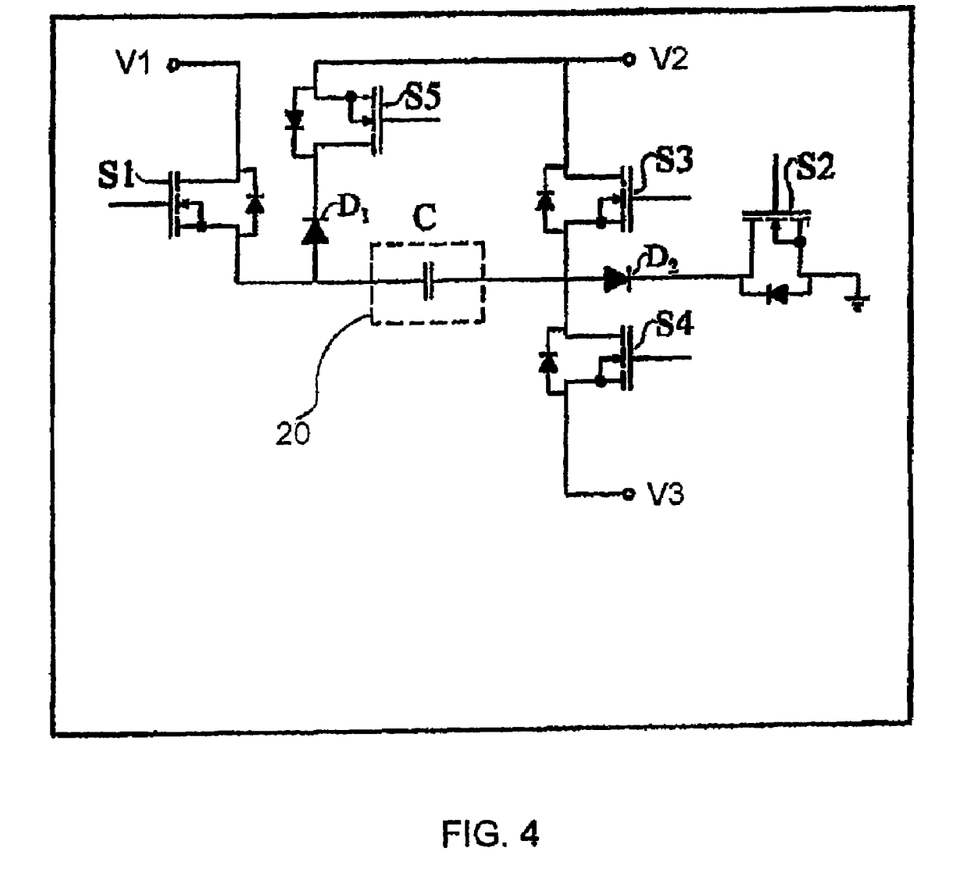
FIG. 4 is a schematic of representative waveform generating electronics, capable of delivering the time-dependent voltage to the electro-optical device, as shown in FIG. 3A.

In embodiments of the invention, suitable voltage waveform generating electronics may include five switches (e.g., MOSFET switching transistors S1, S2, S3, S4, and S5, such as those depicted in the representative circuit diagram shown in FIG. 4) capable of modulating the voltage applied to the electro-optical device in a time frame on the order of 10 nanoseconds. Two high speed diodes and three voltage sources may be used in conjunction with these switches. A first voltage source, for example, may have the capability of applying the baseline voltage, $V_o$ (e.g., from about 30% to about 70% of the quarter wave voltage), to the electro-optical device upon closing S1 and S2 and opening S3, S4, and S5. A second voltage source may have the capability of periodically applying the time-dependent differential voltage $\delta V(t)$ (e.g., having a magnitude from about 5% to about 35% of the quarter wave voltage), such that the total bias voltage, $V(t)$, applied to the electro-optical device is $V_o + \delta V(t)$. This may be accomplished by closing S1 and opening S4 and S5, while periodically opening and closing S2 and S3 with a period substantially equal to the round trip time of the laser energy, in order to establish the first modelocked pulse operating mode.

Thereafter, the electro-optical device may be discharged by closing S3 and S5 and opening S1, S2, changing the value of the effective reflectivity, $R_{eff}$, of the second mirror to substantially 100%. This amplifies the laser energy within the resonator, in a second, amplification operating mode. Extraction or release of the desired laser energy from the apparatus may be achieved upon closing S1 and S4 while opening S2, S3, and S5, thereby applying, to the electro-optical device, the voltage differential between two of the three voltage devices, which is substantially equal to the quarter wave voltage of the device. This applied voltage in turn changes the value of $R_{eff}$ to substantially 0%.

In another embodiment, the present invention is a method for treating a skin pigmentation, such as a tattoo, a portwine stain, or a birthmark. The method comprises exposing pigmented skin of a patient to pulsed laser energy with pulses having a duration of at most about 500 ps and an energy of at least about 100 mj. The pulsed laser energy is generated according to any of the methods, or using any of the apparatuses, discussed above.

In another embodiment, the present invention is a method for removing a tattoo comprising tattoo pigment particles, which may, for example, have a diameter from about 1 to about 10 microns. The method comprises exposing the tattoo pigment particles to pulsed laser energy with pulses having a duration below about twice the acoustic transit time across the tattoo pigment particles. This pulsed laser energy may have pulses with a duration and energy as described above, and/or may be generated according to any of the methods, or using any of the apparatuses, discussed above.

These and other embodiments are apparent from the following Detailed Description.

Figure 2:
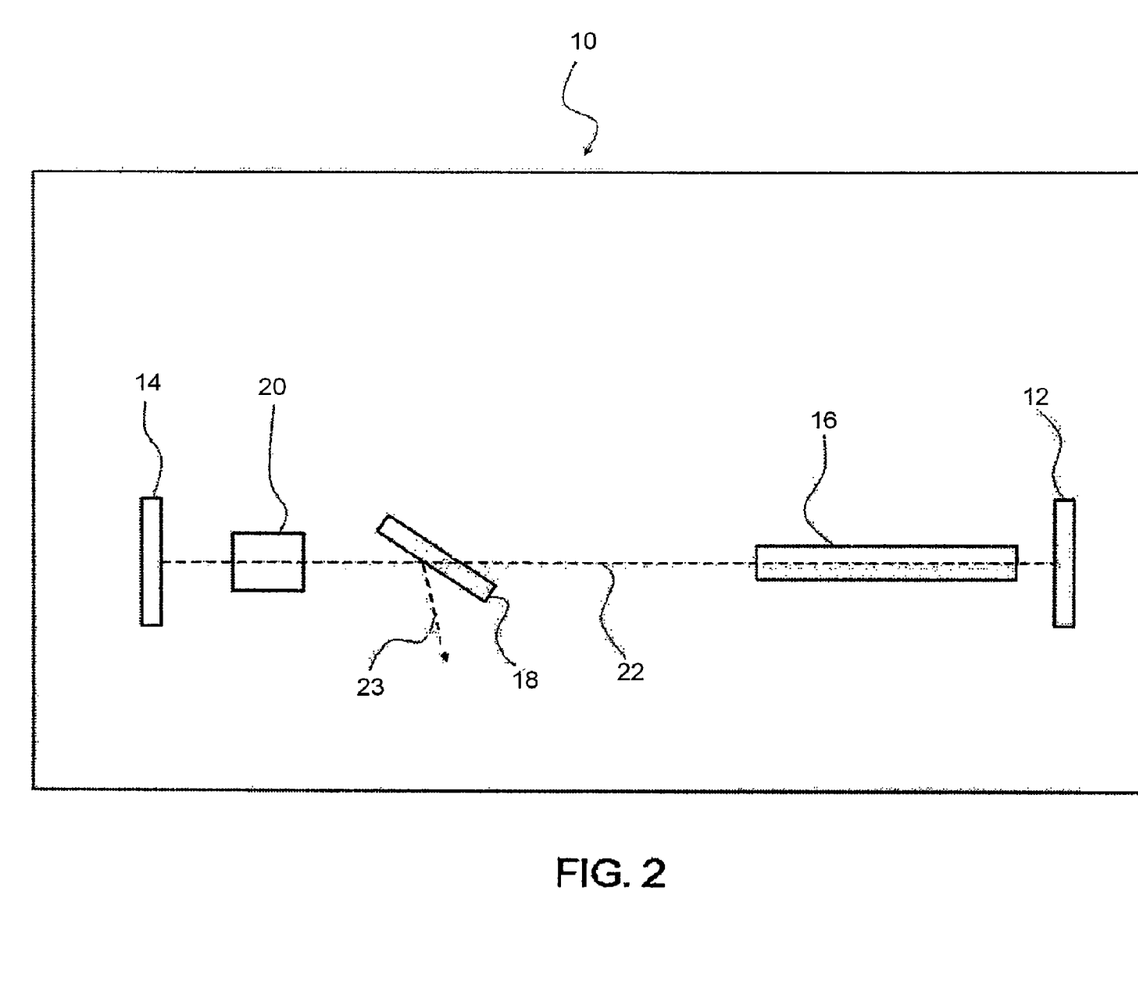
FIG. 2 depicts a representation of a laser emitting apparatus according to the present invention.

The features of the apparatus referred to in the above FIG. 2 are not necessarily drawn to scale and should be understood to present an illustration of the invention and/or principles involved. Some features depicted in the figures have been enlarged or distorted relative to others, in order to facilitate explanation and understanding. The same reference numbers are used in the figures for similar or identical components or features shown in the various embodiments. Laser devices, as disclosed herein, will have configurations, components, and operating parameters determined, in part, by the intended application and also the environment in which they are used.

DETAILED DESCRIPTION OF THE INVENTION

Aspects of the present invention are associated with the ability of laser pulses having a duration of several hundred picoseconds to cause the photomechanical disruption, through the use of sound (or pressure) waves, of tattoo pigment particles and other components of pigmented lesions. Mechanical disruption of the pigment particles facilitates removal of the pigment particles by the body's natural removal processes such as those associated with the immune system. These pulse durations are of the same order as the acoustic transit time across particles having a diameter from about 1 to about 10 microns, which are otherwise sufficiently large to remain stable in skin tissue (e.g., without being cleared by normal immune system responses).

Figure 1:
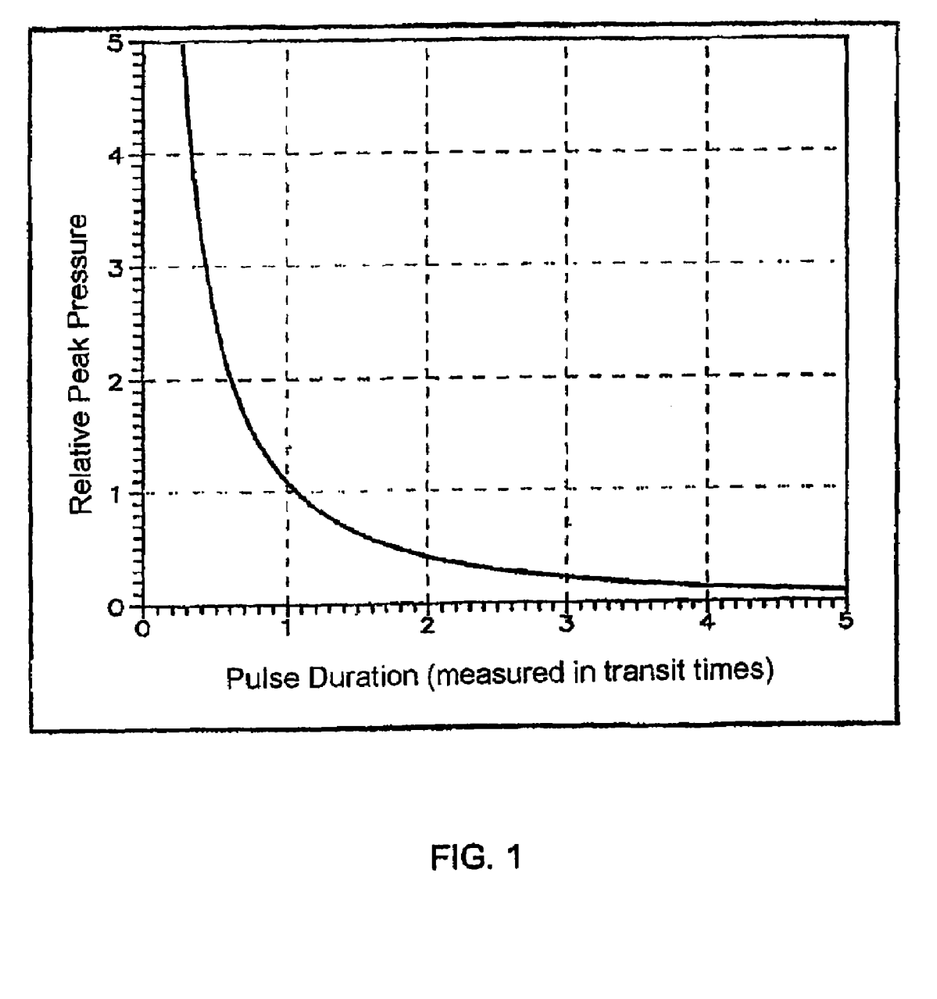
FIG. 1 is a graphical representation showing the relationship between the relative peak pressure within a particle targeted for photomechanical disruption, as a function of pulse duration, measured as a multiple of the acoustic transit time across the particle.

The significance of short pulse duration in photomechanical processes is illustrated graphically in FIG. 1, which shows the non-linear response of peak pressure in a target, as laser pulse duration is reduced. The units of pulse duration, along the x-axis, are normalized to a multiple of the acoustic transit time across a targeted particle, such as a tattoo pigment particle. The acoustic transit time refers to the time required for a sound wave to traverse this target particle. As is apparent from FIG. 1, the photomechanical stress on the target rapidly increases when the irradiating pulse duration decreases to less than about two transit times.

The effect becomes dramatically more pronounced below about one transit time. FIG. 1 therefore illustrates the importance of the ability to operate in the picosecond pulse duration range, in designing a photomechanical treatment or removal protocol for tattoos and other pigmented skin lesions. In fact, as is also clear from FIG. 1, laser pulses having durations of greater than about five times the acoustic transit time induce relatively insignificant peak pressure on the target particle and are therefore relatively ineffective in disrupting small pigmentation particles via the photomechanical mechanism.

Effective apparatuses and methods according to embodiments of the present invention are therefore advantageously capable of delivering laser energy having a pulse duration generally less than about 1 nanosecond, typically less than about 500 picoseconds (ps), and often less than about 250 ps. Common pulse duration values according to some embodiments are in the range from about 100 to about 300 ps. The above values generally represent less than several (e.g., from about one to about three) acoustic transit times for pigmentation particles having a diameter in the range from about 1 to about 10 microns.

Also characteristic of laser energy that is effective for treating or removing skin pigmentations is a relatively high level of energy output. For example, fluences required to achieve significant disruption of pigment particles are generally in the range from about 1 to about 10 j/cm². For viable treatment methods having a treatment area or spot size of a few millimeters in diameter, the required laser output is preferably at least about 100 mj per pulse, and often in the range from about 200 to about 800 mj per pulse.

FIG. 2 depicts a representative embodiment of an apparatus 10 according to the present invention, which is capable of achieving the above pulse duration and energy output parameters, suitable for the effective treatment of pigmented lesions through photomechanical means. Advantageously, the apparatus includes a resonator (or laser cavity) capable of generating laser energy having the desirable pulse duration and energy per pulse, as described herein. The resonator has a characteristic longitudinal or optical axis 22 (i.e., the longitudinal flow path for radiation in the resonator), as indicated by the dashed line. Also included in the representative apparatus shown are an electro-optical device, in this case a Pockels cell 20, and a polarizer 18 (e.g., a thin-film polarizer). During operation, the laser pulse output will be obtained along output path 23.

At opposite ends of the optical axis 22 of the resonator are a first mirror 12 and a second mirror 14 having substantially complete reflectivity. This term, and equivalent terms such as "substantially totally reflective" are used to indicate that the mirrors 12 and 14 completely reflect incident laser radiation of the type normally present during operation of the resonator, or reflect at least 90%, preferably at least 95%, and more preferably at least 99% of incident radiation. The mirror reflectivity is to be distinguished from the term "effective reflectivity," which is not a property of the mirror itself but instead refers to the effective behavior of the combination of second mirror 14, Pockels cell 20, and polarizer 18 that is induced by the particular operation of the Pockels cell 20, as discussed in detail below.

In particular, a laser pulse traveling from lasing or gain medium 16 towards second mirror 14 will first pass through polarizer 18, then Pockels cell 20, reflect at second mirror 14, traverse Pockels cell 20 a second time, and finally pass through polarizer 18 a second time before returning to gain medium 16. Depending upon the bias voltage applied to Pockels cell 20, some portion (or rejected fraction) of the energy in the pulse will be rejected at polarizer 18 and exit the resonator along output path 23. The remaining portion (or non-rejected fraction) of the energy (from 0% to 100% of the energy in the initial laser pulse) that returns to the medium 16 is the "effective reflectivity" of second mirror 14. As explained above, for any given applied voltage to Pockels cell 20, the effective behavior of the combination of second mirror 14, Pockels cell 20, and polarizer 18 is indistinguishable, in terms of laser dynamics, from that of a single partially reflective mirror, reflecting the same non-rejected fraction described above. An "effective reflectivity of substantially 100%" refers to a mirror that acts as a substantially totally reflective mirror as defined above.

Also positioned along the optical axis 22 of the resonator is a lasing or gain medium 16, which may be pumped by any conventional pumping device (not shown) such as an optical pumping device (e.g., a flashlamp) or possibly an electrical or injection pumping device. A solid state lasing medium and optical pumping device are preferred for use in the present invention. Representative solid state lasers operate with an alexandrite or a titanium doped sapphire (TIS) crystal. Alternative solid lasing media include a yttrium-aluminum garnet crystal, doped with neodymium (Nd:YAG laser). Similarly, neodymium may be used as a dopant of pervoskite crystal (Nd:YAP or Nd:YAlO$_3$ laser) or a yttrium-lithium-fluoride crystal (Nd:YAF laser). Other rare earth and transition metal ion dopants (e.g., erbium, chromium, and titanium) and other crystal and glass media hosts (e.g., vanadite crystals such as YVO$_4$, fluoride glasses such as ZBLN, silicaglasses, and other minerals such as ruby) of these dopants may be used as lasing media.

The above mentioned types of lasers generally emit radiation, in predominant operating modes, having wavelengths in the visible to infrared region of the electromagnetic spectrum. In an Nd:YAG laser, for example, population inversion of Nd$^{+3}$ ions in the YAG crystal causes the emission of a radiation beam at 1064 nm as well as a number of other near infrared wavelengths. It is also possible to use, in addition to the treating radiation, a low power beam of visible laser light as a guide or alignment tool. Alternative types of lasers include those containing gas, dye, or other lasing media. Semiconductor or diode lasers also represent possible sources of laser energy, available in varying wavelengths. In cases where a particular type of laser emits radiation at both desired and undesired wavelengths, the use of filters, reflectors, and/ or other optical components can aid in targeting a pigmented lesion component with only the desired type of radiation.

Aspects of the invention also relate to the manner in which the relatively simple apparatus 10, depicted in FIG. 2, is operated to generate laser energy with the desirable pulse duration and energy output requirements discussed above. For example, laser energy from the lasing medium 16 is reflected between the first mirror 12 and second mirror 14 at opposite ends of the optical axis 22 of the resonator. Laser energy emanating from the lasing medium 16 therefore traverses the thin film polarizer 18 and Pockels cell 20 before being reflected by the substantially totally reflective second mirror 14, back through the Pockels cell 20 and polarizer 18.

TIS materials, alexandrite, and other crystals such as Nd:YVO$_4$ exhibit a large stimulated emission cross-section selectively for radiation having an electric field vector that is aligned with a crystal axis. Radiation emitted from such lasing materials is therefore initially linearly polarized, requiring that the polarizer 18 be configured for transmission of essentially all incident radiation by proper alignment with respect to the electric field vector. However, the application of a bias voltage to the Pockels cell 20 can cause elliptical polarization of the exiting radiation, such that the radiation field of the pulse reflected in the second mirror 14 and arriving again at the polarizer 18 will in this case consist of two components with orthogonal electric field vectors being out of phase by some angle.

If the polarizer 18 rejects radiation having an electric field vector that is orthogonal (or perpendicular) to the orientation of the initial electric field vector of radiation from the lasing material 16, the net effect of the combined components (second mirror 14, Pockels cell 20, and polarizer 18) is that of a variable reflectivity mirror. The effective reflectivity, R$_{eff}$, of the second mirror 14 (i.e., the Pockels cell 20 being positioned between that mirror 14 and the polarizer 18), is given by equation (1):

$$R_{eff} = \cos^2\left(\frac{\Pi}{2} V / V_{\lambda/4}\right), \quad (1)$$

where the quantity V$_{\lambda/4}$ is the quarter wave voltage of the Pockels cell 20. The quarter wave voltage refers to the voltage required across the Pockels cell to split the incident radiation into two components having equal intensities and retard the polarization electrical field vector of one component by one-quarter of a wavelength relative to the other component.

Thus radiation, having been reflected at the second mirror 14 and therefore passing twice through the Pockels cell 20 with an applied voltage of V$_{\lambda/4}$, will have its polarization axis rotated 90° and will be completely rejected by polarizer 18. An applied voltage V=V$_{\lambda/4}$ therefore provides an effective reflectivity, R$_{eff}$, of "substantially 0%," meaning that the radiation is either completely rejected by the polarizer 18, or possibly all but a small amount of radiation is rejected (e.g., an amount having an intensity or amplitude generally of less than about 10%, typically of less than about 5%, and often less than about 1%, of its initial intensity or amplitude, I$_o$, prior to the first pass of the radiation through the polarizer 18 and Pockels cell 20). Overall, radiation arriving at the lasing medium 16 after two passes through Pockels cell 20 (and after having been reflected in the second mirror 14) will have an intensity or amplitude, I, given by $$I = I_o \cdot R_{eff}$$

It is recognized that, in various embodiments of the invention, the quarter wave voltage can actually induce a number of possible changes in incident radiation polarization, depending on the particular optical configuration of the apparatus. For example, the use of quarter wave retardation plate positioned between Pockels cell 20 and the second mirror 14 would introduce a double pass polarization axis rotation of 90°, without any applied voltage to the Pockels cell. The effective reflectivity, R$_{eff}$, of the second mirror 14 in this case would be governed by the expression $$R_{eff} = \cos^2\left[\frac{\Pi}{2}(V + V_{\lambda/4})/V_{\lambda/4}\right],$$

where a Pockels cell voltage of 0 would achieve an effective reflectivity of 0%. Application of the quarter wave voltage to the Pockels cell would then introduce an additional 90° of rotation, such that the overall effect would be that of no change in polarization. The effective reflectivity, R$_{eff}$, in this case would be substantially 100%, meaning that the second mirror 14 would act as a substantially totally reflective mirror. It is also recognized that not all lasing media emit linearly polarized radiation or radiation having an electric field vector that is aligned with a crystal axis. For example, Nd:YAG media are non-polarizing. In the case where non-polarizing media are employed, polarizer 18 may establish a given polarization of radiation incident to Pockels cell 20.

Various aspects of the present invention are associated with the advantages obtained when a time-dependent bias voltage, V(t), is applied to an electro-optical device such as the Pockels cell 20. In preferred embodiments of the invention, the time-dependent voltage is equal to the sum of a baseline voltage, V$_o$, and a time-dependent differential or offsetting voltage, δV(t), that varies periodically with a period substantially equal to the round trip time, or twice the time required for the oscillating laser energy to traverse the length of the resonator. The term "substantially equal" in this case refers to deviations between the period of the applied voltage waveform and the round trip time of generally less than about 100 parts per million (ppm), often less than 10 ppm, and preferably less than about 1 ppm.

The application of a time-dependent voltage waveform described above and characterized by equation (2)

$$V(t) = V_o + \delta V(t), \quad (2)$$

where the time-dependent component δV(t) has a period substantially equal to the round trip time of the resonator, allows the resonator to function in a first operating mode, where a modelocked pulse is established in the resonator. Importantly, modelocked oscillation may be obtained without the requirement for an additional modelocking device (or modelocker), such as an acousto-optic modulator, and consequently without the need to adjust resonator length to match a particular resonance frequency.

Thus, the combination of components, together with the applied voltage waveform discussed above, can function essentially identically to a modelocker. In the first modelocked pulse operating mode, the effective reflectivity, R$_{eff}$, of the second mirror 14, is modulated, by modulating the voltage applied to the Pockels cell 20, with a desired frequency (corresponding to a period substantially equal to the round trip time of the oscillating laser energy). The modulated reflectivity over time R(t) is obtained by substituting V$_o$+

δV(t) from equation (2) into the expression for $R_{eff}$ in equation (1) and expanding to obtain $$R(t) = R_o - 2\cos\left(\frac{\Pi}{2}V_0/V_{\lambda/4}\right)\sin\left(\frac{\Pi}{2}V_0/V_{\lambda/4}\right)\left(\frac{\Pi}{2}\delta V(t)/V_{\lambda/4}\right) + \left[\sin^2\left(\frac{\Pi}{2}V_0/V_{\lambda/4}\right) - \cos^2\left(\frac{\Pi}{2}V_0/V_{\lambda/4}\right)\right]\left(\frac{\Pi}{2}\delta V(t)/V_{\lambda/4}\right)^2,$$

where $R_o$, is the initial effective reflectivity of the second mirror 14. From the above expression, it is evident that when operating at $V_o=V_{\lambda/4}$ or $V_o=0$, the linear term vanishes and modulation of the reflectivity is consequently very small. In contrast, the maximum extent or degree of modulation occurs when the baseline voltage $V_o$ is 50% of the quarter wave voltage ($V_o=0.5V_{\lambda/4}$). In preferred embodiments, the baseline voltage $V_o$ is from about 30% to about 70%, and typically from about 40% to about 60%, of the quarter wave voltage of the Pockels cell.

Also, from the above equation for R(t), approximately 30% modulation of the reflectivity can be achieved when the magnitude of δV(t), representing either a positive or a negative deviation from $V_o$, is 20% of the quarter wave voltage. In other embodiments, the time-dependent differential voltage, δV(t), has an amplitude generally from about 5% to about 35%, and typically from about 10% to about 30%, of the quarter wave voltage of the electro-optical device (e.g., the Pockels cell 20). Operation under these parameters, in a first modelocked pulse mode of operation, can therefore mimic the operation of a resonator having an 80% reflecting mirror at one end and also containing a modelocking device such as an acousto-optic device. Modelocking in either case requires a pumping system or device such as a flashlamp (not shown) operating with a sufficient pump rate to the lasing medium 16 to establish the modelocked pulse in the resonator.

In a second (amplification) mode of operation, subsequent to modelocking, the modelocked pulse generated as described above is amplified. Amplification is achieved by applying a constant (first) bias voltage to the Pockels cell 20 such that the second mirror 14 has an effective reflectivity of substantially 100%. In this condition, the modelocked pulse oscillates between two substantially totally reflective mirrors 12 and 14. In embodiments where the effective reflectivity $R_{eff}$ of the second mirror 14 is governed by equation (1) above, a first bias voltage of substantially 0 volts (or substantially complete discharge of the Pockels cell), will provide the desired reflectivity of substantially 100%. In this amplification mode, the laser energy can rapidly increase in amplitude by extracting energy that was previously pumped and stored in the lasing medium 16 during modelocking.

Once the laser energy, oscillating in the resonator under amplification conditions, has reached a desired or maximum amplitude, it can thereafter be extracted. This is achieved by applying a second bias voltage to the Pockels cell 20 such that the second mirror has an effective reflectivity $R_{eff}$ of substantially 0%, to generate pulsed laser energy. In embodiments where the effective reflectivity, $R_{eff}$, of the second mirror 14 is governed by equation (1) above, a second bias voltage equal to the quarter wave voltage of the Pockels cell will achieve the desired reflectivity of substantially 100%. At this point, laser radiation having the desirable pulse duration and energy output described herein, is generated from the apparatus 10 and exits the resonator along output path 23.

Figure 3A:
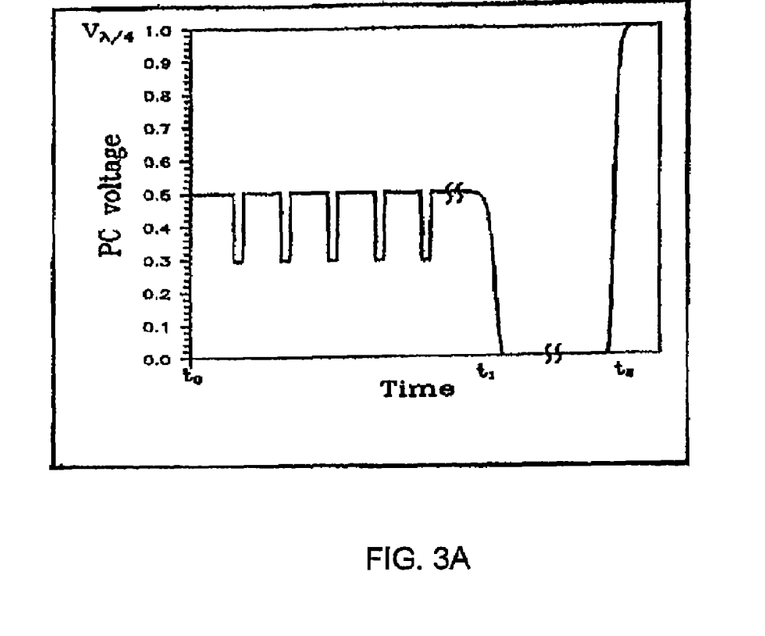
FIG. 3A is a graphical representation of voltage applied over time to an electro-optical device in a laser apparatus, corresponding to a value $V(t)=V_o+\delta V(t)$ between $t_0$ and $t_1$, a value $V(t)=0$ between $t_1$ and $t_2$, and a value $V(t)$ of the quarter wave voltage of the electro-optical device, after $t_2$.

FIG. 3A provides a representation of voltage applied, as a function of time, to an electro-optical device such as a Pockels cell in a laser apparatus, to achieve the operating modes described above. In the time period between $t_0$ and $t_1$, the voltage applied is according to the equation $V(t)=V_o+\delta V(t)$, with the time-dependent differential voltage, δV(t), periodically offsetting an applied baseline voltage, $V_o$. In the particular embodiment of the invention using the voltage waveform shown in FIG. 3A, the baseline voltage is 50% of the Pockels cell quarter wave voltage ($V_o=0.5V_{\lambda/4}$) and the magnitude of the offset is 20% of the Pockels cell quarter wave voltage. This offset occurs periodically with a period equal to the round trip time of laser energy in the resonator.

During operation from time $t_0$ to $t_1$, the pump rate to the gain or lasing medium may be set or adjusted to exceed the threshold for laser oscillation, when $R_{eff}$ (the effective reflectivity of the second mirror) is at or near its highest value. Under these operating conditions, together with the condition that the period of the applied voltage waveform is substantially the round trip time for energy to traverse the resonator as described above, a modelocked pulse can be established within the resonator. The time period between $t_0$ and $t_1$, where a periodic voltage is applied to the electro-optical device, therefore represents the time that the resonator is operating in a first, modelocked pulse mode of operation.

At a time $t_1$, after a steady state modelocked pulse has developed in the resonator, periodic modulation of the applied bias voltage is discontinued and a constant (first) bias voltage is then applied to the electro-optical device, such that $R_{eff}$ is substantially 100%. In the embodiment shown in FIG. 3A, the first voltage, applied at time $t_1$, is 0 volts, meaning that the Pockels cell or other electro-optical device is completely discharged. Under this second, amplification mode of operation, the amplitude of the laser energy within the resonator is allowed to grow rapidly, drawing upon energy previously input into the lasing medium during pumping in the modelocked pulse operating mode, as described above. When the laser energy has reached a desired amplitude, it may then be released as pulsed energy having the pulse duration and energy output as described herein. This release is effected by applying a bias voltage at a later time $t_2$ such that $R_{eff}$ is reduced to substantially 0%. According to the embodiment of FIG. 3A, the applied bias voltage at this time is substantially equal to the quarter wave voltage of the electro-optical device.

Amplification and release (or extraction) of laser energy through the application of first and second (constant) bias voltages, as described above, may also be carried out by applying bias voltages such that $R_{eff}$ beginning at $t_1$ is less than 100%. In the amplification mode of operation, however, $R_{eff}$ is generally greater than 80%, typically greater than about 90%, and often greater than about 95%. Likewise, laser energy may also be released at $t_2$ using an $R_{eff}$ of greater than 0%. For example, a second bias voltage may be applied at $t_2$ such that $R_{eff}$ is generally less than 20%, typically less than 10%, and often less than 5%. In any event, the important consideration is that the device is operated such that $R_{eff}$ is at a relatively high value at $t_1$ and then decreased to a relatively low value at $t_2$, thereby allowing the device to amplify an oscillating laser pulse and thereafter release the amplified laser energy.

In the particular embodiment of the invention characterized by the applied bias voltage waveform shown in FIG. 3A, the voltage required to obtain an $R_{eff}$ value of substantially 100% at $t_1$ is substantially 0 volts. The term "substantially 0 volts" indicates that the electro-optical device may be completely discharged to 0 volts or that the applied voltage will generally be less than 10%, typically less than 5%, and often less than 1%, of the quarter wave voltage of the device. Likewise, in this embodiment of the invention, the voltage required to obtain an $R_{eff}$ value of substantially 0% is substantially equal to the quarter wave voltage. The term "substantially equal to the quarter wave voltage" indicates an applied bias voltage to the electro-optical device of its quarter wave voltage or preferably at least 80%, typically at least 90%, and often at least 95% of its quarter wave voltage.

Also, as explained previously, the Pockels cell or electro-optical device, depending on other components (e.g., a retardation plate) in the apparatus, may require voltages other than 0 and the quarter wave voltage to achieve $R_{eff}$ values of 100% and 0%, respectively. It is also apparent from the cyclical nature of the dependency of $R_{eff}$ on the applied bias voltage, as given by equation (1) above, that higher voltages may be applied to achieve a given effective reflectivity. For example, either 0 volts or the half wave voltage may be applied to obtain $R_{eff}$=100% in equation (1). In general, however, it is preferred that the smallest bias voltage be applied to achieve a given $R_{eff}$. Advantageously, the full range of effective reflectivity values, from 0% to 100%, may be obtained with the application of relatively modest bias voltages in the range from 0 volts to the quarter wave voltage, according to the methods described herein.

Figure 3B:
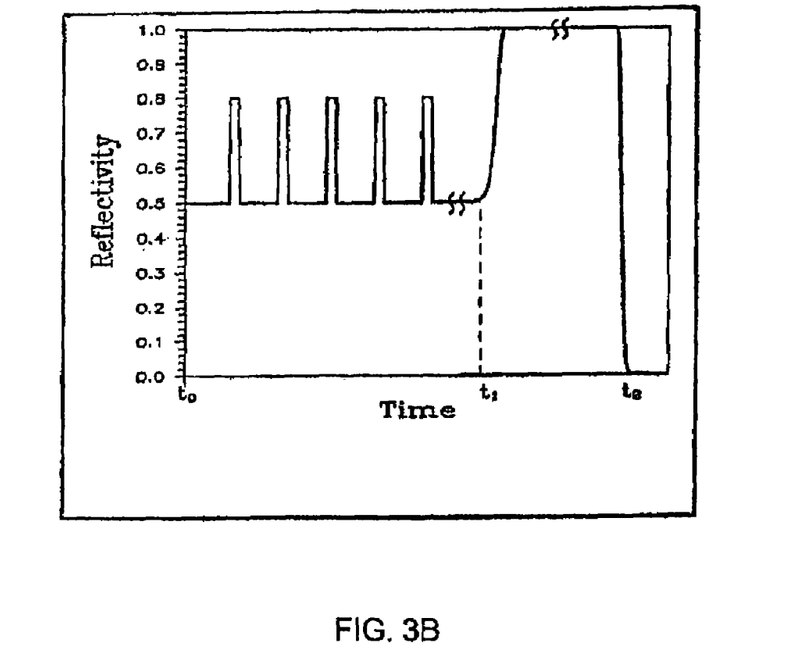
FIG. 3B is a graphical representation of the effective reflectivity over time of the combined mirror, electro-optical device, and polarizer in FIG. 2, with the time-dependent voltage applied to the electro-optical device as shown in FIG. 3A.

FIG. 3B shows, according to one embodiment of the invention, the effective reflectivity over time corresponding to the time-dependent bias voltage waveform applied to the electro-optical device, as shown in FIG. 3A. During the modelocked operating mode from $t_0$ to $t_1$, the effective reflectivity is periodically and positively offset, from a 50% operating value, to a peak value of 80%. The period of the applied voltage waveform matches that of the effective reflectivity waveform, which is the round trip time, or twice the time required for the laser energy to traverse the length of the resonator. At time $t_1$ (at the beginning of the amplification operating mode), when the electro-optical device is discharged, the corresponding value of $R_{eff}$ is 100%. At time $t_2$, when the applied bias voltage is $V_{\lambda/4}$, $R_{eff}$ changes to 0% to release the amplified energy.

The system for generating these waveforms represents another aspect of the present invention, as the electronics require not only a peak voltage of $V_{\lambda/4}$, but also must be capable of a modulation frequency of generally at least about 50 MHz, typically at least about 100 MHz (based on a pulse oscillation time on the order of about 10 nanoseconds), and often at least about 200 MHz. Values of the modulation frequency may therefore be within the representative ranges of from about 50 to about 200 MHz or from about 75 to about 150 MHz. In addition, the switching rise time of the modulation may be approximately 1 nanosecond. FIG. 4 depicts one possible type of waveform generating electronics for producing the bias voltage and $R_{eff}$ waveforms shown in FIG. 3A and FIG. 3B, respectively. The configuration comprises five switches S1, S2, S3, S4, and S5, meeting the requirements set forth above. Preferably, insulated-gate, field-effect transistor (IGFET) switches are employed, such as metal oxide semiconductor field-effect transistor (MOSFET) switches. Two high speed diodes, D1 and D2, and three voltage sources V1, V2, and V3, are also included, as shown in FIG. 4.

Also included in the embodiment of FIG. 4 is a Pockels cell 20, to which the electronic components apply a time-dependent voltage waveform, such as that depicted in FIG. 3A. Electrically, the Pockels cell 20 acts as a capacitor, with a typical capacitance of about 10 picofarads (pF). As described above with respect to FIG. 3A, the waveform generating electronics in the embodiment of FIG. 4 are used for a first mode of operation at a baseline voltage $V_o$ of 0.5$V_{\lambda/4}$ (or the "eighth-wave" voltage, $V_{\lambda/8}$). The baseline voltage is modulated or offset periodically by the time-dependent differential voltage $\delta V(t)$ discussed above and having a magnitude of 0.2$V_{\lambda/4}$ in the particular waveform shown in FIG. 3A. In a subsequent second mode of operation, the waveform generating electronics can be used to discharge the Pockels cell (i.e., apply a constant voltage of 0 volts). Thereafter, a voltage equal to the quarter wave voltage, $V_{\lambda/4}$, of the Pockels cell 20 can be applied.

In view of FIG. 4, at time $t_0$, the initial bias voltage $V_o$ may be applied from voltage source V1 to the Pockels cell 20 by closing S1 and S2 and opening S3, S4, and S5. Under this condition, the electronic configuration shown in FIG. 4 will charge the Pockels cell to the initial bias voltage $V_o$=0.5$V_{\lambda/4}$. In a first, modelocked pulse mode of operation between times $t_0$ and $t_1$, S1 is maintained closed with S4 and S5 open. S2 and S3 are periodically opened and closed with the needed frequency to modulate the bias voltage (e.g., with a period substantially equal to the round trip time of laser energy in the resonator). In particular, closing S3 while opening S2 modulates the baseline voltage with the time-dependent differential voltage, $\delta V(t)$, having a magnitude of offset determined by the voltage from source V2, as shown in FIG. 4. Opening S3 while closing S2 restores the baseline voltage ($V_o$=0.5$V_{\lambda/4}$) from voltage source V1, through the high speed diode D2. The total bias voltage, V(t), applied to the Pockels cell 20 is therefore $V_o$+$\delta V(t)$ during the first mode of operation.

At time $t_1$, a second, amplification mode of operation is established upon closing S3 and S5 and opening S1 and S2. This arrangement discharges the Pockels cell 20 through S3, S5, and the high speed diode D1. Finally, at time $t_2$, closing S1 and S4 while opening S2, S3, and S5 applies the quarter wave voltage, $V_{\lambda/4}$, which is the differential between voltage sources V1 and V3, to the Pockels cell 20, as needed to extract the amplified pulse. Although the Pockels cell capacitance is small, the switching currents reach several amperes as a result of the very fast switching times required. Stray capacitance and/or inductance may impact circuit performance, such that small, tight packaging is desirable.

Apparatuses and methods disclosed herein can therefore achieve a desired quality of pulsed laser energy by alternating between two modes of operation in a single resonator, rather than through the use of two separate resonators. Also, a single Pockels cell, operating in the modes discussed above, can eliminate the need for an additional modelocking device to establish a modelocked pulse within the resonator. Because the Pockels cell does not require operation at a resonant frequency, synchronization with the pulse round trip time is carried out through setting the period of the bias voltage modulation, thereby eliminating the need to adjust resonator length.

The apparatuses and methods disclosed herein are in many cases significantly simplified due to the reduced number of components and/or reduced demands in terms of bias voltage and other operating parameters. Devices may be operated using a modulated waveform according to the requirements and parameters set forth herein, and using the electronic configuration discussed above or various equivalent configurations as would be apparent to one of ordinary skill, having the benefit of the present disclosure. Other embodiments of the invention may involve the introduction of conventional optical components for use in conjunction with the apparatuses disclosed herein, such as shutters or beam attenuators, reflecting prisms or other reflecting components, filters, light focusing components such as concentrators or condensers, collimating lenses, additional polarizers, electro-optical devices, and/or mirrors, etc. These variations are readily contemplated, and the above modifications are therefore well within the purview of one or ordinary skill, having regard for the present disclosure.

In view of the above, it will be seen that several advantages may be achieved and other advantageous results may be obtained. Various changes could be made in the above apparatuses and methods without departing from the scope of the present disclosure. It is intended that all matter contained in this application, including all theoretical mechanisms and/or modes of interaction described above, shall be interpreted as illustrative only and not limiting in any way the scope of the appended claims.

Throughout this disclosure, various aspects are presented in a range format. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 5, from 3 to 6 etc., as well as individual whole and fractional numbers within that range, for example, 1, 2, 2.6, 3, 4, 5, and 6. This applies regardless of the breadth of the range.

The following example is set forth as representative of the present invention. This example is not to be construed as limiting the scope of the invention as other embodiments and aspects of the invention are apparent in view of the present disclosure.

EXAMPLE 1

A laser apparatus as described herein is used to generate pulsed laser energy having a pulse duration of about 100-200 ps with about 500-750 mj/pulse. The laser apparatus includes a resonator with two substantially totally reflective mirrors at opposite ends of its optical axis. An alexandrite crystal lasing medium, a polarizer, and a Pockels cell are positioned along this optical axis. An optical flashlamp is also included for pumping the alexandrite lasing medium, which generates laser energy having a wavelength in the range of 700-950 nm.

The pulsed laser energy described above is generated by pumping the lasing medium and first establishing a modelocked pulse oscillating in the resonator. In the modelocked pulse operating mode, a time-dependent voltage waveform, as described herein, is applied to the Pockels cell. This waveform results from the sum of a constant baseline voltage and a time-dependent differential voltage. The baseline voltage is in the range of 1000-1500 volts (representing 40%-60% of the Pockels cell quarter wave voltage, or 2500 volts) and is negatively offset or modulated by the time-dependent differential voltage, having an amplitude in the range of 250-750 volts (representing 10%-30% of the Pockels cell quarter wave voltage). The period of the resulting voltage waveform is in the range from 5-10 ns and is equal to the round trip time of the oscillating laser energy in the resonator. The voltage applied to the Pockels cell is thus modulated at a frequency in the range from 100-200 MHz.

Subsequently, the modelocked pulse established as described above is amplified by discharging the Pockels cell to essentially 0 volts. Oscillating laser energy is reflected between the mirrors at each end of the resonator, with essentially no losses. This laser energy therefore rapidly increases in amplitude by extracting energy previously pumped and stored in the alexandrite crystal during modelocking. When the laser energy has reached the desired energy level as indicated above, it is extracted from the resonator by applying the quarter wave voltage of 2500 volts to the Pockels cell.

The switching electronics used to operate the laser in modelocked pulse and amplification modes, and finally to extract the amplified pulse as discussed above, comprise five MOFSET switches, two high speed diodes, and three voltage sources having voltages V1 in the range of +1000 to +1500 volts, V2 in the range of +250 to +750 volts, and V3 in the range of −1000 to −1500 volts. The switches, diodes, and voltage sources are configured as shown in FIG. 4.

Laser energy having the pulse duration and energy as described above is applied to a patient undergoing treatment for the removal of a tattoo. This laser energy is applied over the course of a 30-minute treatment session to all areas of the skin having undesired tattoo pigment particles. Photomechanical disruption of these particles is effected using the short pulse duration (below the transit time of a sound wave through the targeted tattoo pigment particles), together with a fluence in the range of 2-4 j/cm$^2$. This fluence is achieved with a laser energy spot diameter of about 5 mm.

Most if not all of the undesired tattoo pigment particles are effectively photomechanically disrupted, destabilized, and/or broken apart using one or two treatments. As a result, the disrupted particles are cleared from the body via normal physiological processes, such as the immune response. The tattoo is thus eventually cleared from the skin with no remaining visible signs. In this manner, various methods described herein are considered methods for treating or removing pigmented particles such as tattoo particles.

What is claimed is:

1. A method for generating pulsed laser energy, the method comprising:

(a) reflecting laser energy generated by a lasing medium between a first mirror at one end of a resonator and a second mirror at the opposite end of said resonator and through a polarizer and an electro-optical device within said resonator and generating a modelocked pulse within the resonator by applying a periodic voltage waveform to the electro-optical device and maintaining an effective reflectivity of the second mirror at 80% or less; and (b) then amplifying the modelocked pulse by applying to said electro-optical device a first constant voltage and maintaining an effective reflectivity of the second mirror at substantially 100%; and (c) then extracting the amplified modelocked pulse from the resonator by applying a second constant voltage to said electro-optical device and maintaining an effective reflectivity of the second mirror at substantially 0%.

2. The method of claim 1, wherein the periodic voltage waveform is equal to the sum of a baseline voltage, $V_o$, and a time-dependent differential voltage, $\delta V(t)$, that varies periodically with a period substantially equal to the twice the time required for said laser energy to traverse the length of said resonator said baseline voltage $V_o$ is from about 30% to about 70% of the quarter wave voltage of said electro-optical device.

3. The method of claim 2, wherein said baseline voltage $V_o$ is from about 40% to about 60% of the quarter wave voltage of said electro-optical device.

4. The method of claim 2, wherein said time-dependent differential voltage, $\delta V(t)$, has an amplitude from about 5% to about 35% of the quarter wave voltage of said electro-optical device.

5. The method of claim 2, wherein said time-dependent differential voltage, $\delta V(t)$, has an amplitude from about 10% to about 30% of the quarter wave voltage of said electro-optical device.

6. The method of claim 1, wherein said electro-optical device is a Pockels cell.

7. The method of claim 1, wherein said first constant voltage is substantially 0 and said second constant voltage is substantially equal to the quarter wave voltage of said electro-optical device.

8. The method of claim 1, wherein said pulsed laser energy has at least about 100 mj/pulse.

9. The method of claim 1, wherein said pulsed laser energy has from about 200 to about 800 mj/pulse.

10. The method of claim 1, wherein said pulsed laser energy has a pulse duration of at most about 500 ps.

11. The method of claim 1, wherein said pulsed laser energy has a pulse duration of at most about 150 ps.

12. A laser apparatus for performing the method of claim 1.

13. A laser apparatus comprising:
(a) a resonator having a first mirror at one end of said resonator and a second mirror at the opposite end of said resonator, wherein both said first mirror and said second mirror are substantially totally reflective; and
(b) a lasing medium, an electro-optical device, and a polarizer along the optical axis of said resonator;
wherein said apparatus generates a modelocked pulse by applying a periodic voltage waveform to the electro-optical device and maintaining an effective reflectivity of the second mirror at 80% or less and then amplifies the modelocked pulse by applying a first constant voltage to the electro-optical device and maintaining an effective reflectivity of the second mirror at substantially 100%.

14. The laser apparatus of claim 13, wherein said electro-optical device is a Pockels cell.

15. A laser apparatus for use in treating tattoos or pigmented tissue comprising a resonator having a first mirror at one end of said resonator and a second mirror at the opposite end of said resonator, wherein both said first mirror and said second mirror are substantially totally reflective, said resonator comprising:
(a) a lasing medium;
(b) a polarizer; and,
(c) an electro-optical device between said polarizer and said second mirror, the electro-optical device responsive to a periodic voltage waveform to maintain an effective reflectivity of the second mirror at 80% or less to generate a modelocked pulse within said resonator, and the electro-optical device responsive to a first constant voltage to maintain an effective reflectivity of the second mirror at substantially 100% to amplify the modelocked pulse;
wherein said lasing medium, said polarizer, and said electro-optical device are positioned along the optical axis of said resonator, and wherein said apparatus is capable of generating pulsed laser energy with pulses having a duration of at most about 500 ps and an energy of at least about 100 mj.

16. The laser apparatus of claim 15, wherein said electro-optical device is a Pockels cell.

17. A laser apparatus comprising:
(a) a resonator having a first mirror at one end of said resonator and a second mirror at the opposite end of said resonator, wherein both of said mirrors are substantially totally reflective;
(b) an electro-optical device and a polarizer along the optical axis of said resonator, wherein said electro-optical device is between said polarizer and said second mirror; and
(c) voltage waveform generating electronics for applying to said electro-optical device a periodic voltage waveform, $V(t)$, equal to the sum of a baseline voltage, $V_o$, and a time-dependent differential voltage, $\delta V(t)$, that varies periodically with a period substantially equal to the twice the time required for said laser energy to traverse the length of said resonator to maintain an effective reflectivity of the second mirror at 80% or less and to generate a modelocked pulse in the resonator, and then applying to said electro-optical device a first constant voltage to maintain said second mirror at an effective reflectivity $R_{eff}$ of substantially 100%.

18. The laser apparatus of claim 17, wherein said electro-optical device is a Pockels cell.

19. The laser apparatus of claim 17, wherein said voltage waveform electronics are capable of (1) initially applying said baseline voltage, $V_o$, to said electro-optical device, prior to applying said time-dependent differential voltage, $\delta V(t)$, and (2) after applying said first constant voltage, applying to said electro-optical device a second constant voltage such that said second mirror has an effective reflectivity $R_{eff}$ of substantially 0%.

20. The laser apparatus of claim 17, wherein said voltage waveform generating electronics comprise:
(a) five MOSFET switching transistors;
(b) two high speed diodes; and
(c) three voltage sources.

21. A method for generating pulsed laser energy comprising:
generating a modelocked pulse within a resonator by applying a periodic voltage waveform to an electro-optical device positioned between the resonator and a mirror and maintaining the effective reflectivity of the mirror at 80% or less; then
amplifying the modelocked pulse within the resonator by applying a first constant voltage to the electro-optical device and maintaining the effective reflectivity of the mirror at substantially 100%; then
extracting the amplified modelocked pulse from the resonator.

22. A laser apparatus comprising:
a resonator having a first mirror at one end of said resonator and a second mirror at the opposite end of said resonator, wherein both of said mirrors are substantially totally reflective;
an electro-optical device and a polarizer along the optical axis of said resonator, wherein said electro-optical device is between said polarizer and said second mirror; and
voltage waveform generating electronics comprising:
(a) five MOSFET switching transistors: S1, S2, S3, S4, and S5;
(b) two high speed diodes: D1 and D2; and
(c) three voltage sources: V1, V2, and V3,
wherein (1) closing S1 and S2 and opening S3, S4, and S5 applies a baseline voltage, $V_o$, to said electro-optical device, (2) closing S1 and opening S4 and S5, while opening and closing S2 and S3 applies a time-dependent differential voltage, $\delta V(t)$, such that a total bias voltage, $V(t)$, applied to said electro-optical device is $V_o + \delta V(t)$, (3) closing S3 and S5 and opening S1, S2, and S4 discharges said electro-optical device and (4) closing S1 and S4 while opening S2, S3, and S5 applies to said electro-optical device a voltage substantially equal to its quarter wave voltage.

23. A method for generating pulsed laser energy comprising
(a) reflecting laser energy generated by a lasing medium between a first mirror at one end of a resonator and a second mirror at an opposite end of the resonator and through a polarizer and one or additional electro-optical devices within the resonator and generating a modelocked pulse within the resonator by applying a periodic voltage waveform to the one or additional electro-optical devices and maintaining an effective reflectivity of the second mirror at 80% or less; and (b) then amplifying the modelocked pulse by applying to the one or additional electro-optical devices a first constant voltage and maintaining an effective reflectivity of the second mirror at substantially 100%, and (c) then extracting the amplified modelocked pulse from the resonator by applying a second constant voltage to the one or additional electro-optical devices and maintaining an effective reflectivity of the second mirror at substantially 0%.

24. A laser apparatus comprising:
(a) a resonator having a first mirror at one end of said resonator and a second mirror at the opposite end of said resonator, wherein both said first mirror and said second mirror are substantially totally reflective; and
(b) a lasing medium, one or additional electro-optical devices, and a polarizer along the optical axis of said resonator;
wherein said apparatus generates a modelocked pulse by applying a periodic voltage waveform to the one or additional electro-optical devices and maintaining an effective reflectivity of the second mirror at 80% or less and then amplifies the modelocked pulse by applying a first constant voltage to the one or additional electro-optical devices and maintaining an effective reflectivity of the second mirror at substantially 100%.

25. A laser apparatus for use in treating tattoos or pigmented tissue comprising a resonator having a first mirror at one end of said resonator and a second mirror at the opposite end of said resonator, wherein both said first mirror and said second mirror are substantially totally reflective, said resonator comprising:

(a) a lasing medium;
(b) a polarizer; and,
(c) one or additional electro-optical devices between said polarizer and said second mirror, the one or additional electro-optical devices responsive to a periodic voltage waveform to maintain an effective reflectivity of the second mirror at 80% or less to generate a modelocked pulse within said resonator, and the one or additional electro-optical devices responsive to a first constant voltage to maintain an effective reflectivity of the second mirror at substantially 100% to amplify the modelocked pulse;
wherein said lasing medium, said polarizer, and said electro-optical device are positioned along the optical axis of said resonator, and wherein said apparatus is capable of generating pulsed laser energy with pulses having a duration of at most about 500 ps and an energy of at least about 100 mj.

26. A method for generating pulsed laser energy, the method comprising:
(a) reflecting laser energy generated by a lasing medium between a first mirror at one end of a resonator and a second mirror at the opposite end of said resonator and through a polarizer and an electro-optical device within said resonator and generating a modelocked pulse within the resonator by applying a periodic voltage waveform to the electro-optical device; and
(b) then amplifying the modelocked pulse by applying to said electro-optical device a first constant voltage and maintaining an effective reflectivity of the second mirror at substantially 100%; and
(c) then extracting the amplified modelocked pulse from the resonator by applying a second constant voltage to said electro-optical device and maintaining an effective reflectivity of the second mirror at substantially 0%.

* * * * *